United States Patent
Lauren

(10) Patent No.: US 8,794,962 B2
(45) Date of Patent: Aug. 5, 2014

(54) METHODS AND COMPOSITION FOR TRACKING JAW MOTION

(75) Inventor: Mark D. Lauren, Amherst, NY (US)

(73) Assignee: 4D Dental Systems, Inc., Amherst, NY (US)

( * ) Notice: Subject to any disclaimer, the term of this patent is extended or adjusted under 35 U.S.C. 154(b) by 768 days.

(21) Appl. No.: 12/759,168

(22) Filed: Apr. 13, 2010

(65) Prior Publication Data

US 2010/0198566 A1 Aug. 5, 2010

Related U.S. Application Data

(63) Continuation-in-part of application No. 12/759,168, filed on May 20, 2009, now abandoned.

(60) Provisional application No. 12/435,940, filed on Apr. 20, 2009, provisional application No. 12/435,940, filed on May 20, 2008.

(51) Int. Cl.
  *A61B 5/103* (2006.01)
  *A61C 19/04* (2006.01)

(52) U.S. Cl.
  USPC ............................... 433/68; 433/69; 600/590

(58) Field of Classification Search
  USPC ...................... 433/68–71, 213; 600/587–590; 700/96–98, 118; 701/1; 523/223, 109; 382/154; 356/12; 348/66
  See application file for complete search history.

(56) References Cited

U.S. PATENT DOCUMENTS

| | | | |
|---|---|---|---|
| 4,836,778 A | 6/1989 | Baumrind et al. | |
| 4,859,181 A | 8/1989 | Neumeyer | |
| 5,143,086 A | 9/1992 | Duret et al. | |
| 5,340,309 A | 8/1994 | Robertson | |
| 5,905,658 A * | 5/1999 | Baba | 703/7 |
| 6,068,482 A * | 5/2000 | Snow | 433/223 |
| 7,182,737 B2 * | 2/2007 | Kim et al. | 600/590 |
| 7,347,690 B2 | 3/2008 | Jordan et al. | |
| 7,362,890 B2 | 4/2008 | Scharlack et al. | |
| 7,471,821 B2 * | 12/2008 | Rubbert et al. | 382/154 |
| 2002/0183959 A1 | 12/2002 | Savill et al. | |

(Continued)

FOREIGN PATENT DOCUMENTS

| | | |
|---|---|---|
| JP | 2005349176 A | 12/2005 |
| JP | 2006110245 A | 4/2006 |
| JP | 2008018094 A | 1/2008 |
| WO | 2007038330 A2 | 4/2007 |

OTHER PUBLICATIONS

International Search Report and Written Opinion of the International Searching Authority dated Jan. 28, 2011 for Great Lakes Orthodontics, Ltd. et al; 8 pages.

*Primary Examiner* — Yogesh Patel

(74) *Attorney, Agent, or Firm* — Hodgson Russ LLP

(57) ABSTRACT

In a method according to an embodiment of the present invention, a plurality of microsphere targets is applied to a surface of a tooth on the upper dentition of a person and a tooth surface of the lower dentition of the person. At least two sets of stereoscopic images are obtained, where the microsphere targets are visible in the field of view of each image. The center position of the beads is photogrammetrically determined in three dimensions for each set using the images taken from perspective positions. The change in bead positions in the sets of stereoscopic images is analyzed to mathematically characterize the jaw motion of the person.

13 Claims, 4 Drawing Sheets

(56) References Cited

U.S. PATENT DOCUMENTS

| | | | |
|---|---|---|---|
| 2006/0127836 A1* | 6/2006 | Wen | 433/24 |
| 2007/0031774 A1* | 2/2007 | Cinader et al. | 433/24 |
| 2007/0160957 A1* | 7/2007 | Wen | 433/213 |
| 2007/0207441 A1* | 9/2007 | Lauren | 433/213 |
| 2007/0231767 A1* | 10/2007 | Sears et al. | 433/8 |
| 2009/0061382 A1* | 3/2009 | Wen | 433/24 |
| 2011/0207074 A1* | 8/2011 | Hall-Holt et al. | 433/29 |

* cited by examiner

METHODS AND COMPOSITION FOR TRACKING JAW MOTION

CROSS-REFERENCE TO RELATED APPLICATION

This application is a continuation-in-part of U.S. application Ser. No. 12/435,940 filed on May 5, 2009 now abandoned, which in turn claims priority to U.S. Provisional Application No. 61/211,941 filed on Apr. 6, 2009 and U.S. Provisional Application No. 61/126,355 filed on May 5, 2008. The disclosures of all of the above applications are incorporated herein by reference.

FIELD OF THE INVENTION

The invention relates to the art of modeling jaw motion, and more particularly to methods for tracking jaw motion and relating the tracked motion to the oral anatomy of a person.

BACKGROUND OF THE INVENTION

Many methods have been employed to measure and record the movement of the human jaw, including: mechanical, electronic, ultrasonic, electromagnetic, and optical techniques. These systems generally have a physical structure ("frame") mounted to each of the maxilla and mandible, with the relative motion between the frames being measured and recorded. Frame-based jaw tracking systems are cumbersome, time-consuming to setup, have limited accuracy, and their presence inherently disrupts an individual's natural jaw movement. In addition, a significant practical limitation is that data obtained from frame-based systems are difficult to register to complete three-dimensional ("3D") models of the dentition. Such registration is required to utilize these data for applications beyond basic motion characterization.

Most recently, optoelectronic systems have been reported. Generally, a mouth-piece or plastic attachments are used to hold optical imaging elements stationary with respect to the mandible and maxilla. These "clutch"-based systems are limited in that they prevent a person from closing their mouth. Additionally, the optical imaging element locations are difficult or impossible to register to the dentition.

Photogrammetry is a method for determining the geometry of objects (e.g., 3D location) from images. Photogrammetry has been used to measure jaw movement using optoelectronic systems by determining the location of targets placed on the face as well as the upper and lower arches.

Devices to aid in tracking jaw motion have been designed, but each of the previous attempts suffers certain shortcomings. Some have described a frame-based system that employs two light detectors (cameras) placed in immovable positions. This system requires an inconvenient calibration step using precisely measured target distances. Another limitation of this system is the inability to register target positions to the dentition. (See, e.g., U.S. Pat. No. 4,836,778 to Baumrind).

Others have disclosed a frame-based system using light-emitting diodes ("LEDs") at the vertices of a triangular fixture that is held outside the mouth by a second support element bonded to the teeth. While jaw tracking data may be taken, target location cannot be accurately or conveniently related to the dentition due to the unknown offset of the LEDs from the teeth. (See, e.g., U.S. Pat. No. 5,143,086 to Duret).

Others propose a method that includes placing 'measurement points' on the dentition. The method assumes that the targets are not precisely on the surface, and since no means are specified for attaching the 'jaw movement measuring points' to the teeth, an elaborate and generalized model is presented to calculate a transform matrix to relate target positions to the dentition. In addition, the basis for this calculation requires that a subjective correspondence be made by the user between the 3D model of the dentition and the position of the targets placed on the teeth, making this procedure difficult to execute and inaccurate. (See, e.g., U.S. Pat. No. 5,905,658 to Baba).

Others describe a photogrammetry-based system that uses plastic 'holding elements' attached to the teeth to position 'reference elements' containing targets outside the oral cavity. This method also has the limitation of being unable to register the target positions to the dentition. (See, e.g., U.S. Pat. No. 4,859,181 to Neumeyer).

Others use cuboidal targets with crosshairs that are held outside the mouth. This method does not provide details as to the target attachment means. Target location data is not amenable to registering to the 3D surface of the teeth. (See, e.g., U.S. Pat. No. 5,340,309 to Robertson).

Other photogrammetry-based jaw tracking systems have been reported in the literature:

Eriksson reports a system using extraoral 5 mm diameter retro-reflective targets that are stroboscopically illuminated. A set of three targets is mounted to the upper and lower front teeth using custom acrylic fixtures, which allow the targets to protrude through the lips and be extraoral. (Eriksson, P. et al.; "Concomitant Mandibular and Head-Neck Movements During Jaw Opening-Closing in Man;" J. Oral Rehab., 1998; (25):859-870)

Kang reports using extra-orally located retro-reflective paper targets placed on a subject's head. Mandibular markers are located on a v-shaped steel rod on the labial surface of the lower incisors. (Kang, D. et al.; "A System for the Study of Jaw Movements;" J. Craniomandib. Practice, 1993; (11)63-67.)

Otake reports a system using infra-red markers attached to custom made jigs shaped for each tooth. (Otake, Y., Suzuki, N., Hattoir, A. et al.; "Real-Time Mandibular Movement Analysis System Using Four-Dimensional Cranial Bone Model;" Systems and Computers in Japan, 2006; 37(8):1216-1226.)

Missaka reports a system that uses custom fabricated maxillary and mandibular intraoral wire frames that extend from the mouth, to then hold white plastic spheres against a black background. (Missaka, R. et al.; "Development of an Experimental Optoelectronic Device to Study the Amplitude of Mandibular Movements;" Braz. Oral Res., 2008; (22)2:151-157.)

In general, the use of light emitting diodes (LEDs) as photogrammetry targets is not ideal. LEDs are relatively large, and require electrical connections in addition to some means of physical attachment to the teeth. Also, the computed location of such targets is inconsistent since LED devices do not emit light in a uniformly spherical manner, and therefore do not have the same optical signature in all viewing directions.

Previous techniques require custom fixtures to mount targets to the upper and lower dentition to keep them stationary with respect to the skull and mandible. Such attachments are time consuming to fabricate, and result in target locations that are not at precisely known locations with respect to the tooth surface. It is therefore difficult or impossible to register the computed target positions to a 3D surface model of the dentition. This is a significant limitation, since many practical applications for jaw motion data require these data to be correlated to the full dentition Previous targets are relatively large and their center locations are less precisely determined than for smaller targets. The required camera setups are large and typically immovable and are not amenable to practical clinical use.

BRIEF SUMMARY OF THE INVENTION

The present invention overcomes these limitations by providing a method to apply photogrammetry targets directly to the tooth surface in a convenient and consistent manner, resulting in known target positions that may be readily registered to complete 3D models of the dentition. No special fixtures or accurately dimensioned jigs are required.

In a method according to an embodiment of the present invention, a plurality of microsphere targets is applied to a surface of a tooth on the upper dentition of a person and a tooth surface of the lower dentition of the person. Patches of microsphere targets may be applied to more than one tooth in each arch (upper and/or lower) of the person. The microsphere targets may be fluorescent. The microsphere targets may be sized between 10 and 1,000 microns. The microsphere targets applied to the upper dentition may be a different color and/or a different size than the targets applied to the lower dentition.

At least two sets of stereoscopic images are obtained, where the microsphere targets are visible in the field of view of each image. Targets are imaged directly on tooth surfaces without tooth transparency complications. Optical filtering provides white targets on a black tooth surface background. The stereoscopic images may include two (or more) images taken simultaneously by two (or more) cameras in fixed spatial relation to each other.

The center position of the beads is photogrammetrically determined in three dimensions for each set using the images taken from perspective positions. The change in bead positions in the sets of stereoscopic images is analyzed to mathematically characterize the jaw motion of the person. For each time increment imaged as a "set," the change in position of the lower beads with respect to a reference or starting position is determined as a Degree of Freedom ("DoF") expression. The captured jaw motion may thereby expressed as a set of DoF expressions.

The invention may also be embodied as a method for creating a digital model of the dentition of a person wherein a digital record of three dimensional tooth surface anatomy that overlaps and extends continuously from the bead locations, termed "extended anatomy" is obtained. The surface of the extended anatomy is shelled (expanded normal to the surface) by the average radius of a bead.

This allows the maxillary and mandibular shelled extended anatomy to be accurately registered to the corresponding upper and lower target locations at any jaw position, such as the reference position used to determine the DoF expressions. The extended anatomy may then be directly animated using the DoF expressions computed from the microsphere locations.

An object of this invention is to provide a convenient jaw tracking method that produces data that is readily registered to conventional 3D models of the dentition.

Another object of the invention is to provide a composition and associated application method for microsphere target material to be applied directly to the teeth for imaging.

A further object of the invention is to provide an inexpensive hand-held imaging device suitable for use in the dental clinic for taking non-invasive jaw tracking measurements.

DESCRIPTION OF THE DRAWINGS

For a fuller understanding of the nature and objects of the invention, reference should be made to the following detailed description taken in conjunction with the accompanying drawings, in which.

DETAILED DESCRIPTION OF THE INVENTION

Figure 1:
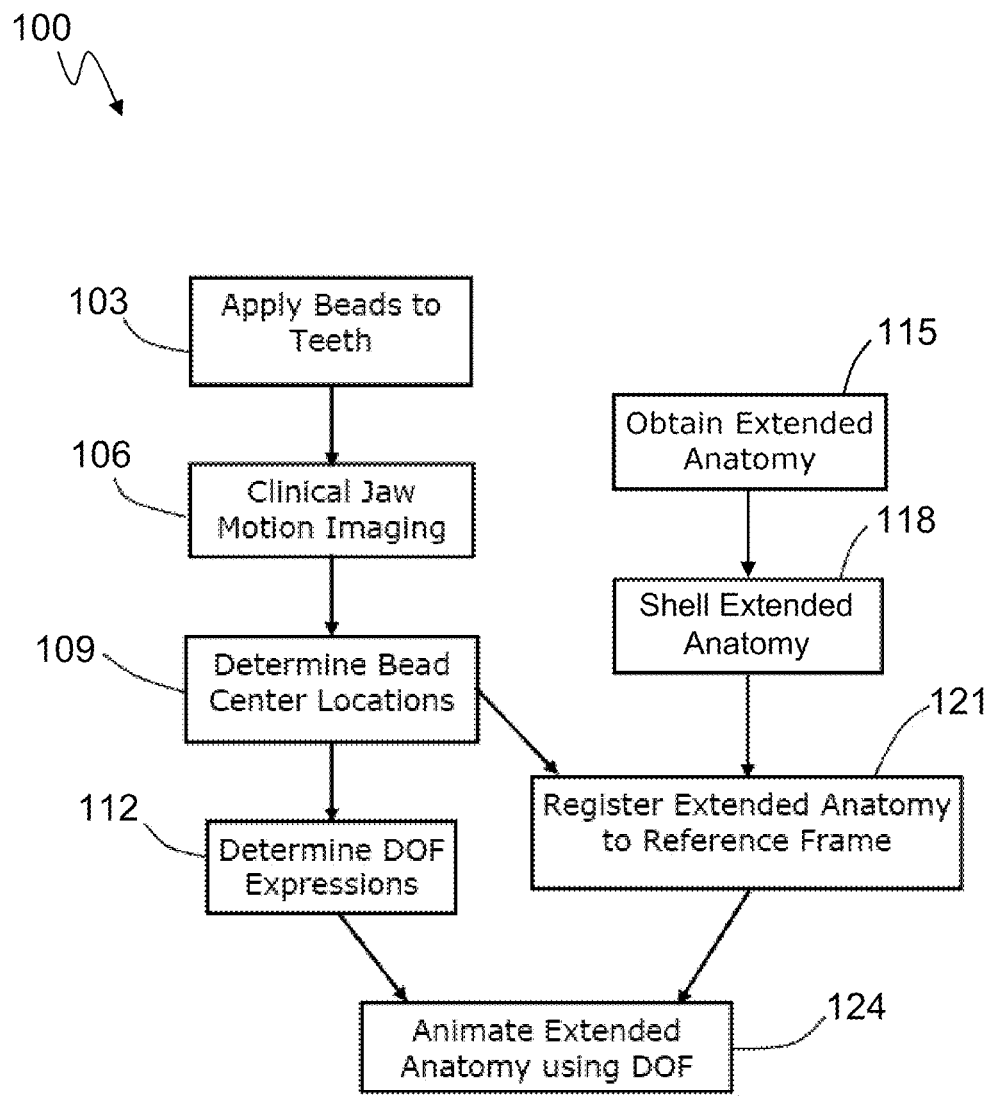
FIG. 1 is a flowchart depicting a method according to an embodiment of the present invention.

FIG. 1 depicts a method 100 according to an embodiment of the present invention in which the jaw motion of a person is tracked and digitized. Steps 103-112 describe a basic jaw tracking method, and steps 109 and 115-124 describe using of the basic tracking data to animate overlapping or extended 3D oral anatomy. A plurality of microsphere targets (such as those available from Polysciences, Inc. of Warrington, Pa.) is applied 103 to a surface of a tooth on the upper dentition of the person and a tooth surface of the lower dentition of the person. The microsphere targets may also be referred to herein as microspheres and/or beads. Any number of microsphere targets sufficient for tracking may be applied to the tooth surface in a "patch." In a non-limiting example, each tooth surface may have 1-10 beads or more. Patches may be applied to more than one tooth in each arch (upper and/or lower) of the person. For example, a patch of microsphere targets may be applied to the surfaces of two teeth in the upper arch and one tooth in the lower arch of a person.

In an embodiment according to the invention, the microsphere targets may be fluorescent. For example, the targets may absorb excitation light in the range of between 400 and 500 nm and emit light in the range of between 500 and 600 nm.

In another embodiment according to the invention, the microsphere targets applied to the upper dentition may be a different color than the targets applied to the lower dentition. In this manner, the upper and lower dentition may be more easily discerned during image analysis.

The microsphere targets may be sized between 10 and 1,000 microns. The microsphere targets applied to the upper dentition may be a different size than the targets applied to the lower dentition. In this manner, the upper and lower dentition may be more easily discerned during image analysis.

The microsphere targets may be applied using a blue-tinted polymer material (further described below). As such, the fluorescent spheres are surrounded by a blue film on the teeth. Optical filtering in front of a digital imaging camera may block incident blue excitation radiation and pass the green radiation emitted from the beads (in an embodiment using beads which fluoresce green light) for imaging. In this way, using a monochrome digital camera, the target beads image as white against a black (blue film) background. The system provides excellent contrast between the targets and the surrounding blue film, eliminating tooth transparency issues.

At least two sets of stereoscopic images are obtained 106. Each of the stereoscopic images includes a field of view in which the microsphere targets of the upper and lower teeth are visible. In this way, the microsphere targets are imaged as photogrammetry targets. The stereoscopic images may include two images taken simultaneously by two cameras in fixed spatial relation relative to each other. In another embodiment, three cameras in fixed relation to each other are used to capture three simultaneous images of the dentition from three different views. The cameras need not be fixed spatially to the person or the dentition.

The center position of the beads is determined in three dimensions for each set 109 using the images taken from perspective positions. The sets of stereoscopic images are analyzed 112 to mathematically characterize the jaw motion of the person.

Each of the at least two sets of stereoscopic images is taken at a different time during the jaw motion of the person, and thus, the sets of stereoscopic images capture the jaw in different positions. A plurality of sets may be captured in order to determine the motion of the jaw in fine increments. For example, the jaw motion may be captured at a rate of up to 20 sets per second or more. For each time increment imaged, the change in position of the lower beads with respect to a reference or starting position is determined 112 as a Degree of Freedom ("DoF") expression. The captured jaw motion may thereby expressed as a set of DoF expressions.

The invention may also be embodied as a method for creating a digital model of the dentition of a person. Referring again to FIG. 1, a plurality of microsphere targets may be applied 103 to a surface of a tooth on the upper dentition of the person and a tooth surface of the lower dentition of the person. Multiple sets of stereoscopic images of the microsphere targets are obtained 106. The 3D center locations of the microsphere targets are determined 109 for each set of images such that a 3D model (a "point cloud") of the microsphere target positions is obtained.

A digital record of three dimensional tooth surface anatomy that overlaps and extends continuously from the bead locations, termed "extended anatomy," may be obtained 115 using conventional means of scanning stone models or impressions, or by intraoral scanning or other techniques known in the art. The digital record may include, for example, a 3D model of the full upper and/or lower arch of the person.

Since the centers of the microsphere targets all lie a fixed and generally known distance (for example, an average microsphere radius) from the tooth surface, the targets may be readily registered to the extended anatomy after expanding ("shelling") 118 the tooth surfaces by a constant value. In this manner, the center of each microsphere target in the digital model will substantially correlate to the shelled surfaces of the teeth in the digital record.

The shelled extended anatomy is then registered 121 to the 3D target positions in the reference or starting position used to determine the DoF expressions 112. The DoF expressions, computed from the bead data 112, may then be used to animate the extended anatomy 124.

Figure 2:
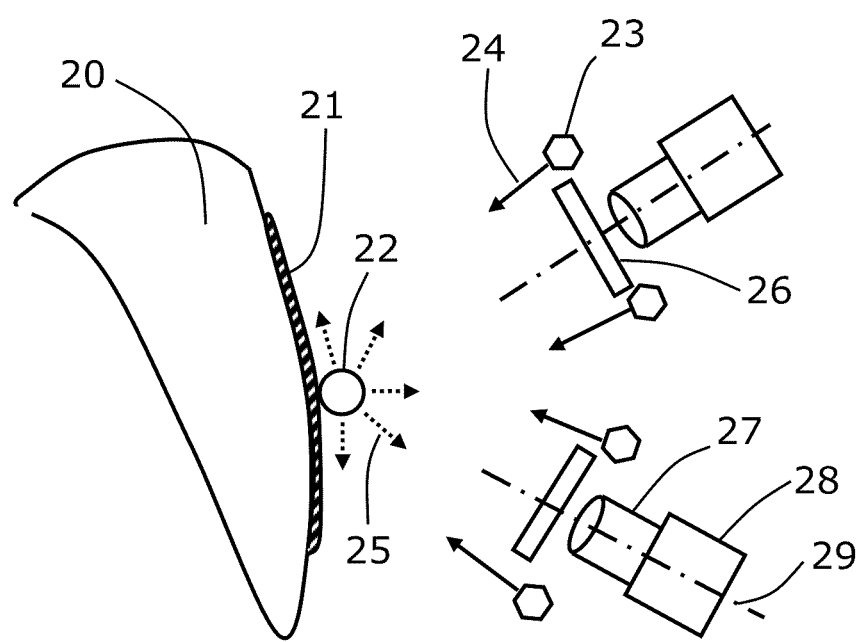
FIG. 2 is a schematic drawing of a single fluorescent microsphere bead and an imaging system according to another embodiment of the present invention.

FIG. 2 is a non-scaled schematic drawing of a single fluorescent microsphere bead and the imaging system. A tooth 20 is shown in cross-section. A blue polymer film 21 lies on the anterior surface of the tooth, with an attached fluorophore-containing microsphere 22. Blue light emitting diode (LED) emitters 23 directed at the tooth surface, emit blue excitation light 24. The fluorescent bead absorbs the blue light and emits green light 25. Element 26 is an optical filter that blocks the blue excitation light and passes the green light emitted by the bead. Filter 26 may be a bandpass filter in the 500-600 nm range or a green dichroic filter mounted in front of lens 27 and monochrome digital camera unit 28. The optical axis of the camera system is shown as 29.

Figure 3:
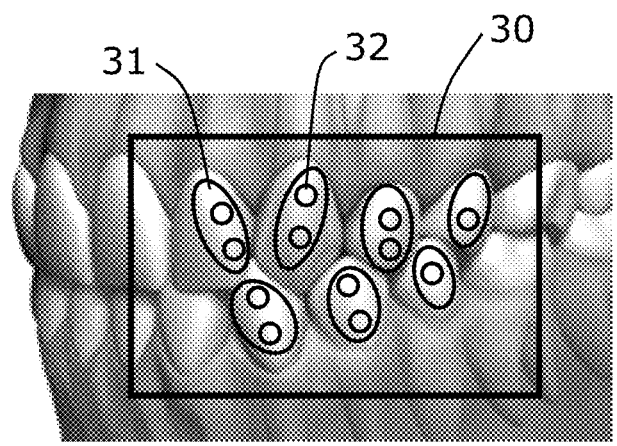
FIG. 3 depicts a field of view for an imaging system according to another embodiment of the present invention.

FIG. 3 shows a field of view 30 in one embodiment of an imaging system, which is approximately 30×40 mm. This field is sufficient to image four to six teeth in a quadrant, typically from the lateral incisor to the bicuspids on one side of the mouth. A film area 31 is indicated, containing beads 32. Microsphere beads are shown larger than actual size.

Figure 4:
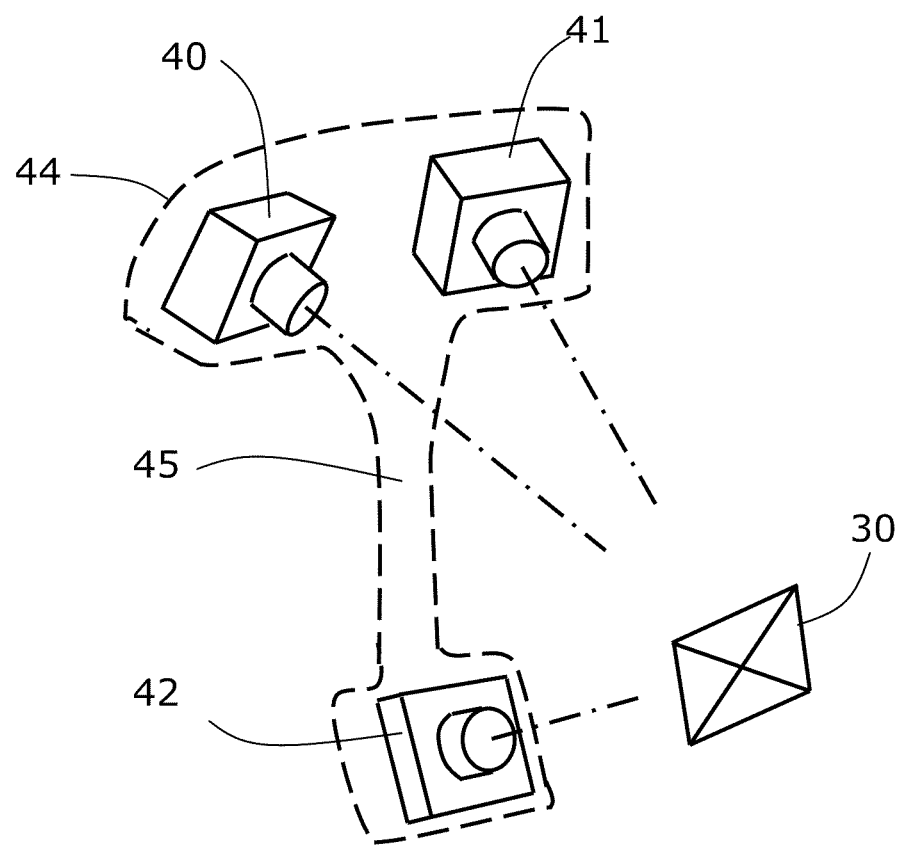
FIG. 4 shows an imaging unit suitable for use in an embodiment of the present invention.

FIG. 4 shows the general design of an imaging unit or device used to capture sets of stereoscopic images of the beads. Three synchronized monochrome digital cameras 40, 41, 42 are mounted in fixed positions with respect to each other. Each camera images substantially the same field of the mouth 30 which may be approximately 30×40 mm. The cameras may be enclosed by a plastic housing 44 with an interconnecting region 45 which can serve as a handle. The illuminating LEDs and laser alignment elements are not shown for simplicity.

Bead and Carrier Composition

Polymer microspheres are used as photogrammetry targets. The microspheres may be fluorescent. Typical polymer materials may be polystyrene and polyethylene. The microspheres, or beads, may range from about 10 to 1,000 microns in diameter. The polymer spheres may have a fluorophore either on the bead surface or internal to the bead. Typical fluorophores include fluoresein, fluorescein isothiocyanate, and Nile red.

In one embodiment, target beads contain a fluorescent material which absorbs blue excitation light in the 400-500 nm range and emits green light in the 500-600 nm range.

The microspheres may be applied to the teeth as part of a composition suitable for brush-on application. The composition also comprises a biocompatible volatile carrier component. The carrier may be, for example, ethanol. The carrier may be a water-soluble liquid to allow easy cleaning in the mouth. The composition further comprises a polymer mixed with the carrier. Suitable polymer solutes include compatible polymers such as polyvinylpyrolidone (PVP), cellulose derivatives, polyvinyl alcohol, and polyethylene glycol.

In use, when the composition is applied to a tooth surface, the carrier will evaporate leaving a the microspheres behind on the tooth surface trapped in a thin polymer film. The carrier may be selected to be sufficiently volatile so as to form a film in a short period of time (e.g., less than 30 seconds). The composition may be sufficiently viscous to minimize flowing on the tooth surface.

The film covering the beads may be relatively thin (about 3 microns) compared to a typical bead (about 250 microns diameter). While the film is drying, the beads settle by gravity to effectively result in direct contact with the tooth surface. The bead carrier composition is brushed onto tooth or soft tissue surfaces as a patch area which may be approximately 4×8 mm, and which may contain approximately 1-10 or more beads per patch.

In another embodiment, a biologically safe volatile carrier such as ethanol is used to form a film of some polymer component upon evaporation. A small amount of water, ranging from 1-15% may be added to provide a more aqueous environment for minimizing aggregation of the beads. This allows the use of surfactants such as sodium dodecyl sulfate to be used to assist with dispersing the beads in the carrier, minimizing clumping.

Non-Limiting Example Carrier Composition:
 8% high molecular weight PVP ($1.6 \times 10^6$ MW) in 95% ethanol
 1% Erioglacine
 0.2% sodium dodecyl sulfate
 Microsphere bead concentration of 10,000 beads/ml
 The viscosity of the carrier is 80 cp.

This example blue carrier composition results in approximately 20 beads per patch area of 30 mm² brushed onto a tooth surface using a 4 mm wide flat soft nylon brush.

Microsphere polymer beads may also be colored and non-fluorescent and serve as photogrammetry targets. Different fluorophores may be used for maxillary and mandibular targets, and the different emission spectra used to distinguish upper and lower arch targets. Different diameter beads may also be used to distinguish targets on the upper and lower arches.

Bead Application Methods

In another embodiment, beads are suspended in an ethanol-based carrier to facilitate brushing onto a surface. The bead concentration is adjusted to provide a desired surface density of beads. Film formation may take approximately 5-10 seconds.

In another embodiment, beads may be applied to tooth surfaces using a two-step process. This method results in targets with significantly enhanced imaging properties, having minimal colored film covering its surface. First, a film of blue or other colored base without targets is applied to the teeth. After drying, the beads, in a non-colored or clear carrier, are applied on top of the colored film. The beads are then trapped in a clear film that blends with the colored layer. This provides an application wherein the bead is isolated on a colored background. In practice, the solvent in the clear carrier dissolves some of the blue film, resulting in the target beads effectively resting directly on the tooth surface.

In another embodiment, beads may be applied to tooth surfaces using a manual applicator that dispenses a controlled number of beads. Beads may be individually placed on an initially deposited film. Beads may also be applied as pre-mounted to a thin transferable film that effectively contains beads in a prescribed geometric pattern.

A non-interfering cheek retractor system may be used to keep the lips apart during application of the beads and imaging. Beads may be applied to tooth or soft tissue surfaces. The patient may be positioned such that the teeth to be used are generally horizontal. This may be done by first positioning the head straight back and then tilting slightly to one side or the other. This provides good access for coating and provides a gravitational component towards the facial aspect of the teeth. After the film dries, the person may be returned to a normal erect posture. The head and jaw may be positioned in any orientation during imaging. In an embodiment, beads are applied to three upper and three lower teeth, from the lateral incisor to the first or second bicuspid.

Imaging

Photogrammetry methods are well known in the art. For the methods of this invention, imaging may involve capturing three two-dimensional ("2D") monochrome digital images of fluorescing microsphere polymer beads from different perspectives to facilitate computing the 3D location of the bead centers. Three digital cameras may be synchronized to image at a rate up to approximately 20 Hz or more.

Analogous to the time-based frames of a conventional digital or analog video, wherein each frame comprises a 2D image, each time-based frame according to an embodiment of the present invention comprises the 3D locations of the upper and lower beads, represented as a point cloud computer file such as an *.igs or *.dxf.

Incident light for fluorescence is provided by light emitting diodes (LEDs). When using fluorescein-based beads, a blue or violet led light source may be used. The light source may have optical filtering that only allows wavelengths below approximately 500 nm to pass.

Imaging units may be fitted with optical filters to only pass the fluorescing wavelengths, for example from 500 to 600 nm for fluorescein. In this way, the blue excitation light is blocked and only the green emitted light from the beads is imaged. The blue background film images as black. Fluorescing bead targets are thereby imaged as white on a black background. The method thereby provides for the direct imaging of targets placed on a tooth surface without tooth transparency interferences.

Non-Limiting Example Of Camera Specifications:
Light source—blue LEDs
Camera—2 MP monochrome digital camera
Lens—17 mm focal length
Optical filters—a bandpass filter in the 500-600 nm range (e.g., those available from Semrock Inc., Rochester, N.Y.)
Working distance—20 cm.

At a distance of 20 cm from the mouth, the example system provides a field of view of approximately 30×40 mm. This is sufficient to image at least 3 upper and three lower teeth, from the lateral incisor to the first or second bicuspid on one side of the mouth.

While monochrome cameras provide resolution to individual pixels and are suitable for photogrammetry applications, color imagers may also be used. Color cameras provide the ability to differentiate upper and lower targets using different fluorophores.

An example imaging device is shown schematically in FIG. 4. The three cameras, mounted inside the imaging device, are configured to simultaneously capture bead images at a rate up to approximately 20 Hz or more. The imaging system is designed to have a 30×40 mm field of view at a distance of approximately nine inches.

The three camera units may be separated from each other by approximately nine inches, making for a small and light imaging device that is readily hand-held. The micro-size targets reduce the size of the required imaging system, making it practical for the dental clinic. A laser alignment system may be included on the camera to assist the user in correctly positioning the imaging unit. The alignment laser may emit radiation at 635 nm which may be blocked by the camera's bandpass filter.

The imaging device may have independent controls for the alignment beams and data acquisition. The images captured by the device may be transferred in real-time to a computer for storage and further processing.

Clinical jaw motion imaging is performed with the lips held apart using a cheek retractor. The camera may be positioned approximately 20 cm from the beads using laser alignment beams. In an embodiment, the beads are imaged from a general aspect perpendicular to the cuspids to provide a field with significant dimension in orthogonal directions. Data capture may start from centric occlusion, or a fully closed position of the jaws. This permits the first captured image to be used as a reference position for the DoF determinations.

A single image, taken under both ambient and blue light, may be used to confirm whether a particular bead is on the upper or lower arch. In the fully closed position, there can be considerable vertical overlap of the teeth. In general, the number of teeth used and the pattern of application can be used to readily differentiate upper and lower targets.

Software may also be used to automatically determine two populations of targets based on detecting which points remain fixed with respect to each other during motion, and which points do not.

Computing Bead Center Locations

Using well known photogrammetry methods, the captured images for each time increment may be used to determine the 3D center locations of the beads for each time increment. Subpixel target marking may be used for improved accuracy. Commercially available software (such as PhotoModeler from EOS Systems of Vancouver, Calif.), may be used for automatic target marking, referencing targets between a set of 2D bead images, and computing 3D centers of the beads. A point cloud computer file is created for each time increment, such as a *.igs or *.dxf file comprising the 3D locations of the beads. A complete captured motion sequence may therefore be represented by a set of *.dxf files, with each file representing incremental 3D positions of the upper and lower beads. Each *.dxf file in a sequence is considered an individual frame.

Determination of Degree of Freedom (DOF) Expressions

This step involves using the bead location data to compute mathematical expressions to describe the incremental change in position of the lower jaw with respect to a fixed maxilla for a clinically captured jaw motion sequence. A number of mathematical schemes and approaches may be used to achieve the same incremental motion expressions. The precise mathematical pathway followed to derive relative motion expressions from the time-based bead locations is not important to the execution of this invention.

A reference position or frame, comprising the 3D location of the target beads, is first defined to serve as a starting point for the relative motion expressions. Any image in a motion sequence may serve as a reference image. The reference position or frame is generally taken to be the first position in a captured sequence or with the mouth in centric occlusion. If the upper and lower targets cannot be automatically distinguished from each other, it is necessary to tag or identify the upper or lower targets in the reference frame. This may be done by having target centers appear as separate objects on a computer screen, and selecting or highlighting using a mouse. The location of a particular bead may be confirmed using the clinical image taken under both ambient and blue light. A fully defined reference frame comprises known upper and lower 3D bead locations.

A number of methods may be used to differentiate upper and lower targets. Pattern recognition methods based on a prescribed application technique may be used. Target size or emission spectra may also be used.

It is not necessary to identify the upper and lower targets in the remaining data set. During the target data registration process, as long as the targets do not move a significant amount from the previous frame, software may be used to search for, identify, and confirm target correspondence.

After fully defining a reference position, the upper or maxillary target positions in a second (or other) frame are registered to the upper bead positions in the reference frame. The upper data in the second frame now coincides with the reference upper, and the lower data is displaced from the reference lower. This displacement is expressed as a six degree of freedom ("DoF") function, comprising three translational and three rotational terms. A DoF expression is derived for each frame in a captured sequence. Continuing this process for the remaining frames in a time sequence produces a set of DoF expressions that describe incremental change in position of the lower arch for the imaged sequence.

In another embodiment, the upper and lower bead locations are used to construct separate upper and lower bead-derived surfaces. Each frame would then comprise an upper and lower surface. Surfaces may be more conveniently used for registration and DoF determinations than individual point locations.

These basic DoF data represent the 3D movement of the mandible. Previously, such raw jaw tracking data was limited to tracing 2D line curves in different planes. Modern ultrasonic and electromagnetic 3D jaw tracking methods produce generally similar data. The DoF expressions derived from these previous methods are limited to describing jaw motion, as they cannot be accurately or reliably related to the 3D surface of the teeth.

Extended Anatomy

Extended anatomy includes the surface that underlies and extends out from the locations of the upper and lower bead positions. Extended anatomy may be obtained by intraoral scanning, or digitizing a dental cast or impression or other techniques commonly known in the art.

Registration of Extended Anatomy to Reference Frame

A feature of the present invention is the ability to easily register target locations with 3D models of the dentition. No special fixtures or accurately dimensioned jigs are required. The ability to easily relate bead location data to 3D models of the dentition is important to executing practical applications of these data beyond basic jaw tracking.

The background film may be thin (approximately 3-5 microns as measured by scanning electron microscopy) compared with an example average bead radius of approximately 150 microns, and may be ignored for registration purposes. The diameter of polymer microspheres has a certain size distribution. The 2 sigma variation in diameter, for diameters in the 200-400 um range, is about 20 microns, which is significantly greater than an average film thickness. In addition, since the beads rapidly settle in an alcohol-based carrier, they fall the very short distance through the underlying carrier to the tooth surface by gravity during film formation. The bead centers may therefore be assumed to lay one bead radius from the tooth surface.

Since the centers of the beads lay one bead radius from the tooth surface, the computed target locations (bead centers) do not precisely correspond with the point of attachment of the bead to the surface. The true tooth surface lays one bead radius away from the target centers in some unknown direction. Accurate registration of extended anatomy to the reference target positions requires more precise correspondence than a bead radius.

To facilitate correspondence between reference target locations and the tooth surface, the extended anatomy is shelled by one bead radius to have its surface correspond with the bead centers. The shelling process grows the surface in a direction normal to the surface. Shelling is commonly performed and has become a very rapid manipulation using 3D models.

No transforms are required to relate jaw motion positional data with the 3D anatomy of the dentition. The process has no subjective aspects, and is therefore amenable to automatic data processing. This is another significant advantage of this invention to existing art since the present invention provides a more accurate and automated process.

Use of DoF Expressions to Animate Extended Anatomy

A feature of the jaw motion data obtained by method according to the present invention is the ability to relate to and animate a person's 3D oral anatomy. Following registration to a reference frame, the extended anatomy may be animated using the DoF expressions computed from the bead movement data. This forms the basis for the practical application of these data beyond characterizing jaw movement.

Applications may include any device or oral appliance whose design requires occlusion of the teeth such as crowns, bridges, and dentures. The following examples illustrate two such applications Non-Limiting Example Applications 1. Enhanced Crown Design For enhanced crown design, the extended oral anatomy refers to the 3D surface anatomy associated with the preparation for the new tooth, its adjacent teeth, and the antagonist teeth in the opposing arch. Animating the occlusal surface of antagonist teeth provides the means to generate a dynamic surface which represents the locus of antagonist tooth positions. Designing crowns, using computer aided design, against this surface reduces the interferences when the crown is fitted in the mouth.

2. Custom Condylar Inserts

The range of motion of natural jaw motions may be captured and converted to a set of left and right-side condylar eminence geometries. This locus of positions may be used to fabricate a patient-specific insert to be placed in a dental articulator to allow the device to duplicate the natural jaw motions of an individual.

Although the present invention has been described with respect to one or more particular embodiments, it will be understood that other embodiments of the present invention may be made without departing from the spirit and scope of the present invention. Hence, the present invention is deemed limited only by the appended claims and the reasonable interpretation thereof.

What is claimed is:

1. A method of tracking jaw motion of a person, comprising the steps of:
   (a) applying a plurality of microsphere targets to a tooth surface of the upper dentition of the person and a tooth surface of the lower dentition of the person;
   (b) obtaining at least two sets of stereoscopic images of the microsphere targets on the upper and lower teeth surfaces, wherein each set is captured at a different time during jaw motion; and
   (c) analyzing the at least two sets of stereoscopic images to mathematically characterize jaw motion of the person.

2. The method of claim 1, wherein each set of stereoscopic images comprises two or more images of the microsphere targets taken from different points of view.

3. The method of claim 2, wherein each set of stereoscopic images comprises three images of the microsphere targets taken from different points of view.

4. The method of claim 1, wherein the microsphere targets are individually applied to the teeth.

5. The method of claim 1, wherein the microsphere targets are contained in a liquid composition.

6. The method of claim 5, wherein the plurality of microsphere targets are applied to the tooth surfaces by brushing the liquid composition onto the tooth surfaces.

7. The method of claim 1, wherein the microsphere targets have a diameter of between 10 and 1,000 microns.

8. The method of claim 7, wherein the microsphere targets applied to the tooth surface of the upper dentition are selected to be a different size than the microsphere targets applied to the tooth surface of the lower dentition.

9. The method of claim 1, wherein the microsphere targets are fluorescent.

10. The method of claim 9, wherein the microsphere targets applied to the tooth surface of the upper dentition are selected to be a different color than the microsphere targets applied to the tooth surface of the lower dentition.

11. The method of claim 1, wherein analyzing the images includes determining the three-dimensional centers of the targets.

12. The method of claim 11, wherein jaw motion is characterized by using the target centers to determine degree of freedom expressions for each image set.

13. The method of claim 1, wherein the at least two sets of stereoscopic images of the microsphere targets on the upper and lower teeth surfaces are obtained using an imaging system.

* * * * *

UNITED STATES PATENT AND TRADEMARK OFFICE
CERTIFICATE OF CORRECTION

| | | |
|---|---|---|
| PATENT NO. | : 8,794,962 B2 | Page 1 of 1 |
| APPLICATION NO. | : 12/759168 | |
| DATED | : August 5, 2014 | |
| INVENTOR(S) | : Lauren | |

It is certified that error appears in the above-identified patent and that said Letters Patent is hereby corrected as shown below:

Title page, after Related U.S. Application Data items (63) and (60) should read:

--(63) Continuation-in-part of application No. 12/435,940, filed on May 5, 2009, now abandoned.

(60) Provisional application No. 61/211,941, filed on Apr. 6, 2009, provisional application No. 61/126,355, filed on May 5, 2008.--

Signed and Sealed this
Ninth Day of December, 2014

Michelle K. Lee
*Deputy Director of the United States Patent and Trademark Office*